(12) United States Patent
Chen

(10) Patent No.: US 7,380,480 B1
(45) Date of Patent: Jun. 3, 2008

(54) SAFETY NEEDLE DEVICE FOR TATTOOING BODY AND EYEBROWS

(76) Inventor: Cheng-Kun Chen, 235 Chung-Ho Box 8-24, Taipei (TW)

( * ) Notice: Subject to any disclaimer, the term of this patent is extended or adjusted under 35 U.S.C. 154(b) by 0 days.

(21) Appl. No.: 11/710,057

(22) Filed: Feb. 23, 2007

(51) Int. Cl.
*B43K 5/00* (2006.01)
(52) U.S. Cl. ........................................ 81/9.22; 604/198
(58) Field of Classification Search ................ 604/192, 604/195–198; 81/9.22
See application file for complete search history.

(56) References Cited

U.S. PATENT DOCUMENTS 5,741,290 A * 4/1998 Hsieh ........................ 606/186

6,505,530 B2 * 1/2003 Adler et al. ................. 81/9.22

* cited by examiner

*Primary Examiner*—Sam Chuan Yao
*Assistant Examiner*—Bradley J Osinski

(57) ABSTRACT

A safety needle device for tattooing body and eyebrows comprises a body; a needle; a needle cover for receiving the needle; a holding cover combinable to a rear end of the needle cover; a needle clamper received in the holding cover for clamping the needle at one end and engaged to the body at another end thereof; and a telescopic element installed between the holding cover and a rear end of the needle clamper. The body has a joint; one end of the joint has a combining portion and the needle clamper has a combining block; two wedge recesses are formed at two sides of a connection area between the combining block and the joint. In the unused state, the needle and the needle clamper are received within the needle cover. An interior of the needle cover is formed with a protecting space for receiving the needle.

8 Claims, 7 Drawing Sheets

SAFETY NEEDLE DEVICE FOR TATTOOING BODY AND EYEBROWS

FIELD OF THE INVENTION

The present invention relates to needle devices, and particularly to a safety needle device for tattooing body and eyebrows.

BACKGROUND OF THE INVENTION

In the prior art safety needle device for tattooing body and eyebrows, the needle is arranged at a front end thereof. The needle is exposed from the tattoo machine, which will pierce the skin of a person with dye therein. In such a process, the blood or bacteria will pollute the needle. This will possibly pollute other users or pierce the operator in faulty operation. Thus there is an eager demand for a novel design which can improve the prior art defects.

In one improvement, a middle section is installed between the tattoo body and a handle. A movable portion is installed in the middle section for pivotally installing with a sleeve. The sleeve is installed with a needle which passes through the handle for exposure from the tattoo machine. The sleeve and the middle section can stop pollutants and can be changed.

In another improvement, a hollow head receiving a plurality of needles has a sleeve for exposing a single needle.

However, although the prior art can prevent the dye or other undesired objects from flowing back and the needle can be changed, normally, the needle is exposed from. It is possible that the needle will pierce other people and the pollutant blood or bacteria will transfer to the body of such a person. Thus, the prior art deficiencies of the tattoo needle still exists. Moreover, the structure for preventing the dyes, blood, or bacteria from flowing back is too complicated to be made and the cost is high.

SUMMARY OF THE INVENTION

Accordingly, the primary object of the present invention is to provide a safety needle device for tattooing body and eyebrows which comprises a body; a needle; a needle cover for receiving the needle; a holding cover combinable to a rear end of the needle cover; a needle clamper received in the holding cover for clamping the needle at one end and engaged to the body at another end thereof; and a telescopic element installed between the holding cover and a rear end of the needle clamper. The body has a joint; one end of the joint has a combining portion and the needle clamper has a combining block; two wedge recesses are formed at two sides of a connection area between the combining block and the joint. In the unused state, the needle and the needle clamper are received within the needle cover. An interior of the needle cover is formed with a protecting space for receiving the needle.

The various objects and advantages of the present invention will be more readily understood from the following detailed description when read in conjunction with the appended drawing.

DETAILED DESCRIPTION OF THE INVENTION

In order that those skilled in the art can further understand the present invention, a description will be provided in the following details. However, these descriptions and the appended drawings are only used to cause those skilled in the art to understand the objects, features, and characteristics of the present invention, but not to be used to confine the scope and spirit of the present invention defined in the appended claims.

Figure 1:
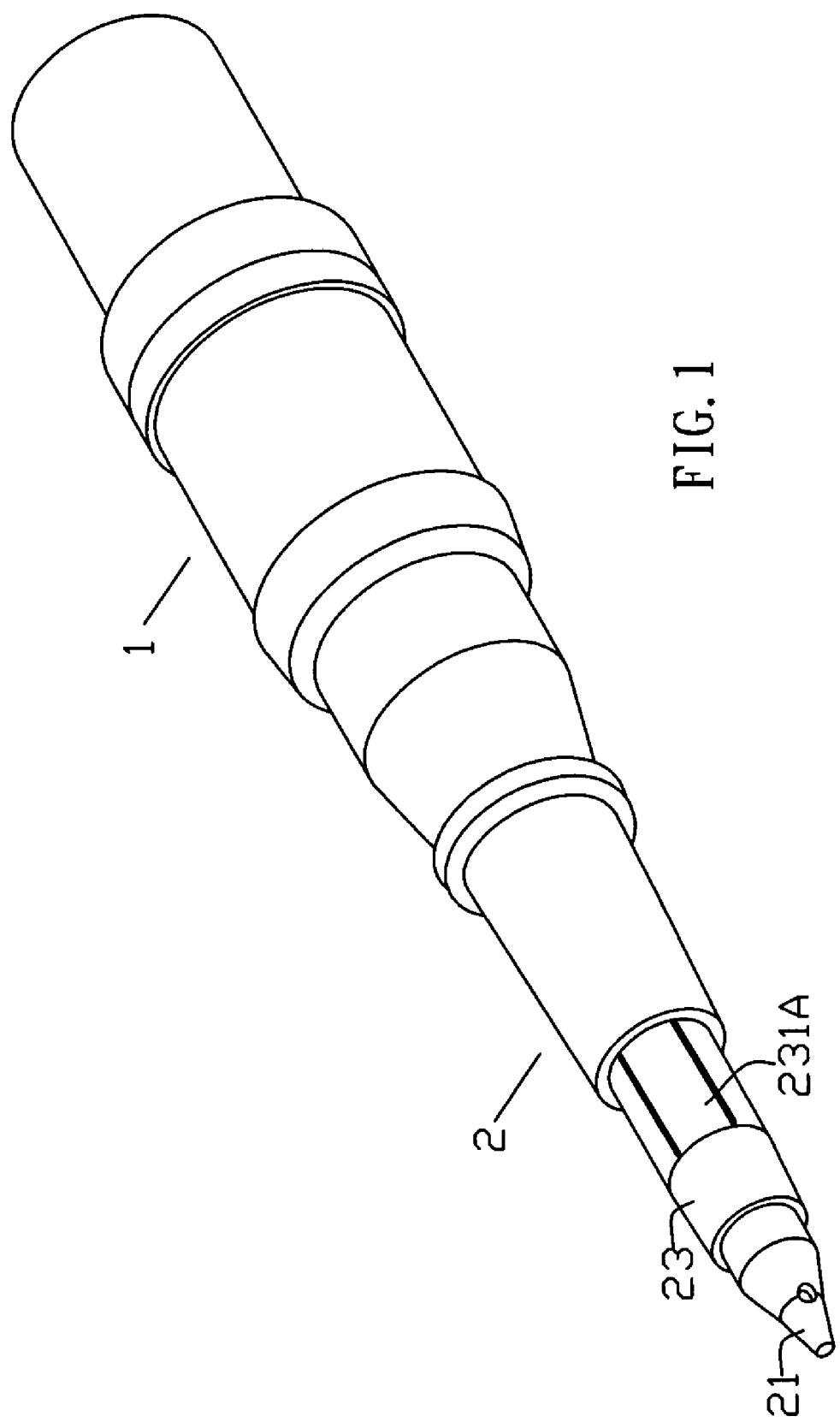
FIG. 1 is an schematic view of the first embodiment of the present invention.
Figure 2:
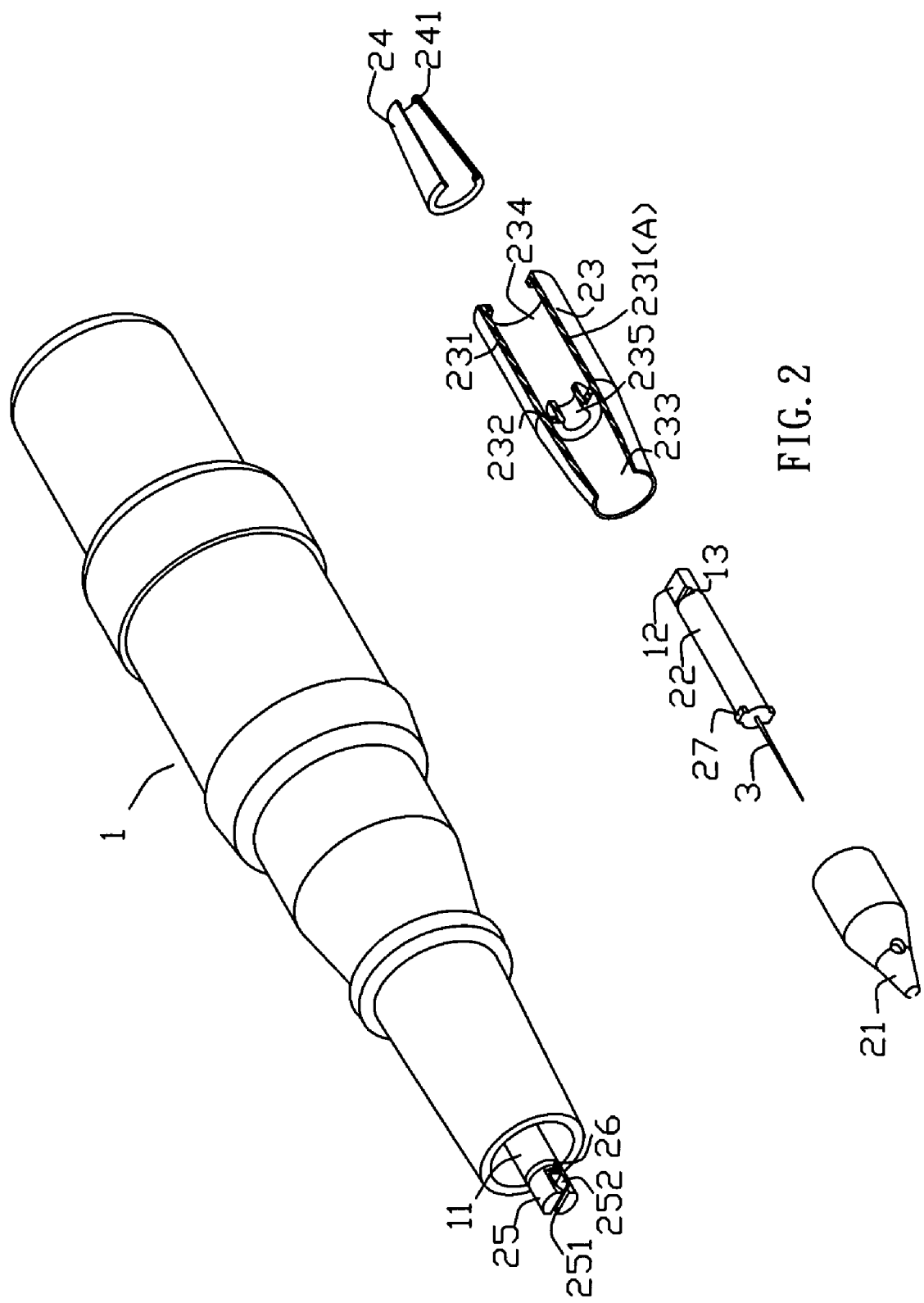
FIG. 2 is an exploded view of the first embodiment of the present invention.
Figure 3:
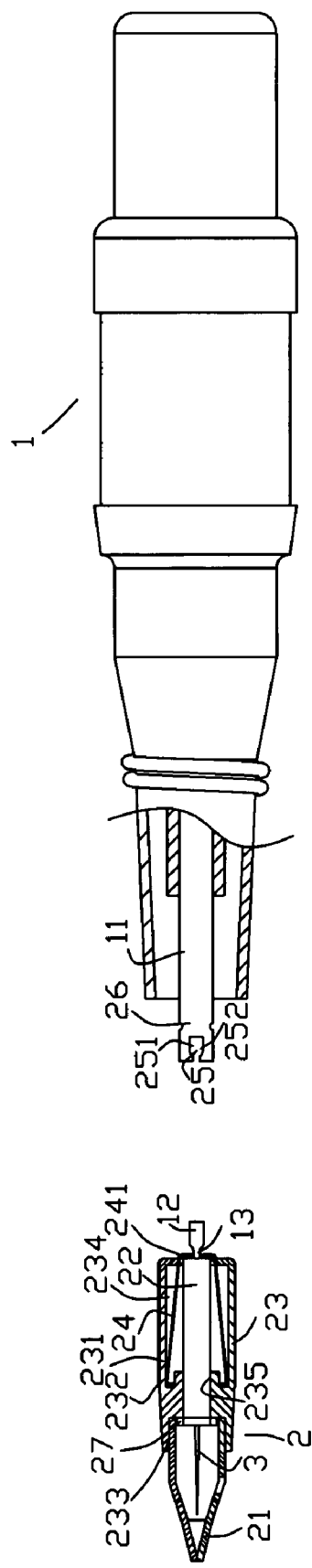
FIG. 3 is a schematic view showing the combination of the body and the safety needle assembly according to the present invention.

With reference to FIGS. 1, 2, and 3, the structure of the present invention will be described herein.

A body 1 has a joint 11. One end of the joint 11 has a combining portion 25 and an annular trench 26.

A safety needle assembly 2 can be connected to joint 11 of the body 1. The safety needle assembly 2 has a needle cover 21, a needle 3, a needle clamper 22, a holding cover 23, and a telescopic element 24 so that the needle 3 will not pierce other people, as shown in FIGS. 2 and 3.

The needle cover 21 is engaged to the holding cover 23 so as to form a protection space for protecting the needle 3.

The holding cover 23 has an outer tube 231 for being held by users. A periphery of the outer tube 231 has a plurality of axial ribs 231 so that the safety needle assembly 2 can be separated from or combined with the body 1 rapidly. A needle seat 232 is installed within the outer tube 231. The needle seat 232 divides the outer tube 231 into a first chamber 233 and a second chamber 234. A hole 235 is formed in the needle seat 232 for communicating the first chamber 233 and second chamber 234. The needle clamper 22 is movable in the hole 235. The first chamber 233 serves for combining the needle cover 21. The second chamber 234 serves for receiving the telescopic movement of the needle 3 so as to combine with the body 1.

The needle cover 21 is a long cylinder. One end of the needle clamper 22 serves to clamp the needle 3. Two limiting blocks 27 are formed at two sides of the needle clamper 22 at one end near the needle 3 for controlling the needle 3 to move forwards to expose out or to move backwards for storage. When the needle clamper 22 retracts into the first chamber 233 to a rearmost position, the two limiting blocks 27 resist against a wall of the needle seat 232 at the first chamber 233. Another end of the needle clamper 22 opposite to the end having the limiting blocks 27 has a combining block 12. Two wedge recesses 13 are formed at two sides of a connection area between the combining block 12 and the needle clamper 22.

Figure 2B:
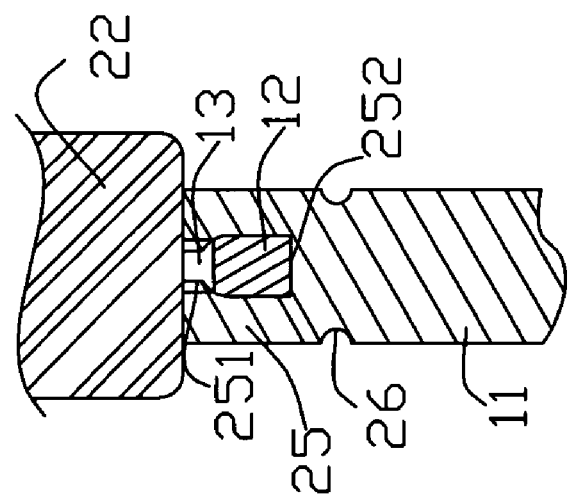
FIG. 2B is a partial cross sectional view showing the combination of the body and the safety needle assembly according to the present invention.
Figure 2A:
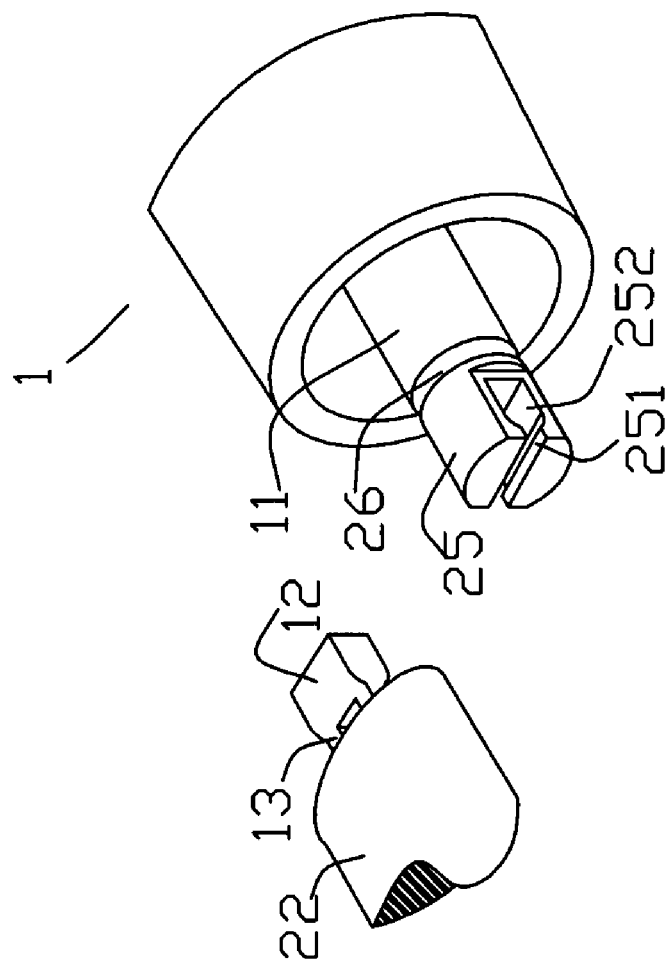
FIG. 2A is a schematic view showing the combination of the body and the safety needle assembly according to the present invention.

The combining portion 25 has at least one wedge portion 251 and an embedding groove 252 therein corresponding to the combining block 12 and wedge recess 13 of the needle clamper 22 so that the body 1 can be combined to the safety needle assembly 2 rapidly, referring to FIGS. 2(A) and 2(B).

Besides, the telescopic element 24 is an elastic element which is compressible, preferably, it is a rubber with two thicker ends or flexible thermal setting plastics with a wavelike shape. One end of the telescopic element 24 has a larger size and resists against one end surface of the needle seat 232 at the second chamber 234 of the holding cover 23. Another end of the telescopic element 24 has a smaller size and has an embedding portion 241 which can be embedded into the embedding groove 252 of the needle clamper 22 so that liquid can be sealed without draining out from the second chamber 234.

Figure 4:
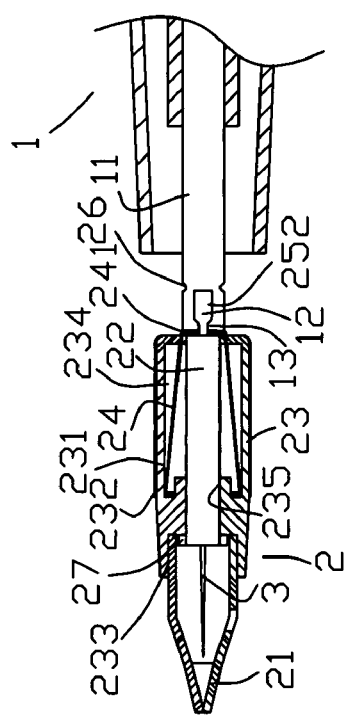
FIG. 4 is a schematic view showing that the needle of the present invention is not pushed outwards.
Figure 5:
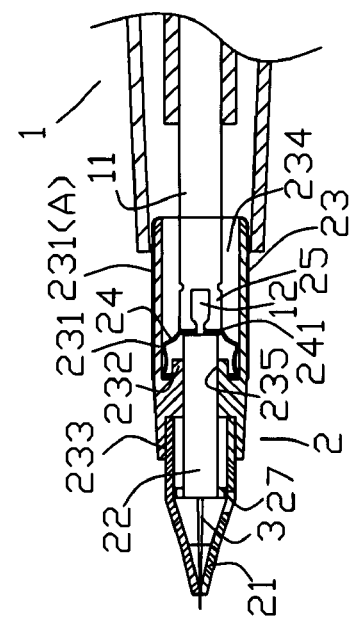
FIG. 5 is a schematic view showing the needle of the present invention has been pushed outwards.

Referring to FIGS. 4 and 5, the states about the storage and exposure of the needle 3 are illustrated. As illustrated in the drawings, the safety needle assembly 2 is engaged to the joint 11 of the body 1 by using the combining portion 25 of joint 11 so that the needle 3 and the needle clamper 22 are fixed. Then, the telescopic element 24 resists against the holding cover 23 and the annular trench 26 of the needle clamper 22 so that normally, the needle 3 can be received within the needle cover 21, as shown in FIG. 4. When it is desired to expose the needle 3 from the needle cover 21, the safety needle assembly 2 pushes the body 1. The action of pushing the needle cover 21 and the holding cover 23 will cause the needle 3 to expose out and is compressible, or the shape of the telescopic element 24 is changed so as to generate a return force, as shown in FIG. 5. After the needle is used, it is only necessary to release the engagement of the safety needle assembly 2 and the body 1. The telescopic element 24 will push the needle cover 21 and the holding cover 23 so that the needle 3 is received within the needle cover 21.

When the needle 3 is not used, it is received in the needle cover 21 so as to retain a clean state without polluting by dirt. Moreover, the user can use the present invention easily and conveniently.

Furthermore one end of the telescopic element 24 resists against one end of the needle cover 21 so that the liquid is sealed by the body 1 and safety needle assembly 2 without draining out. No dye will flow backwards.

Figure 6:
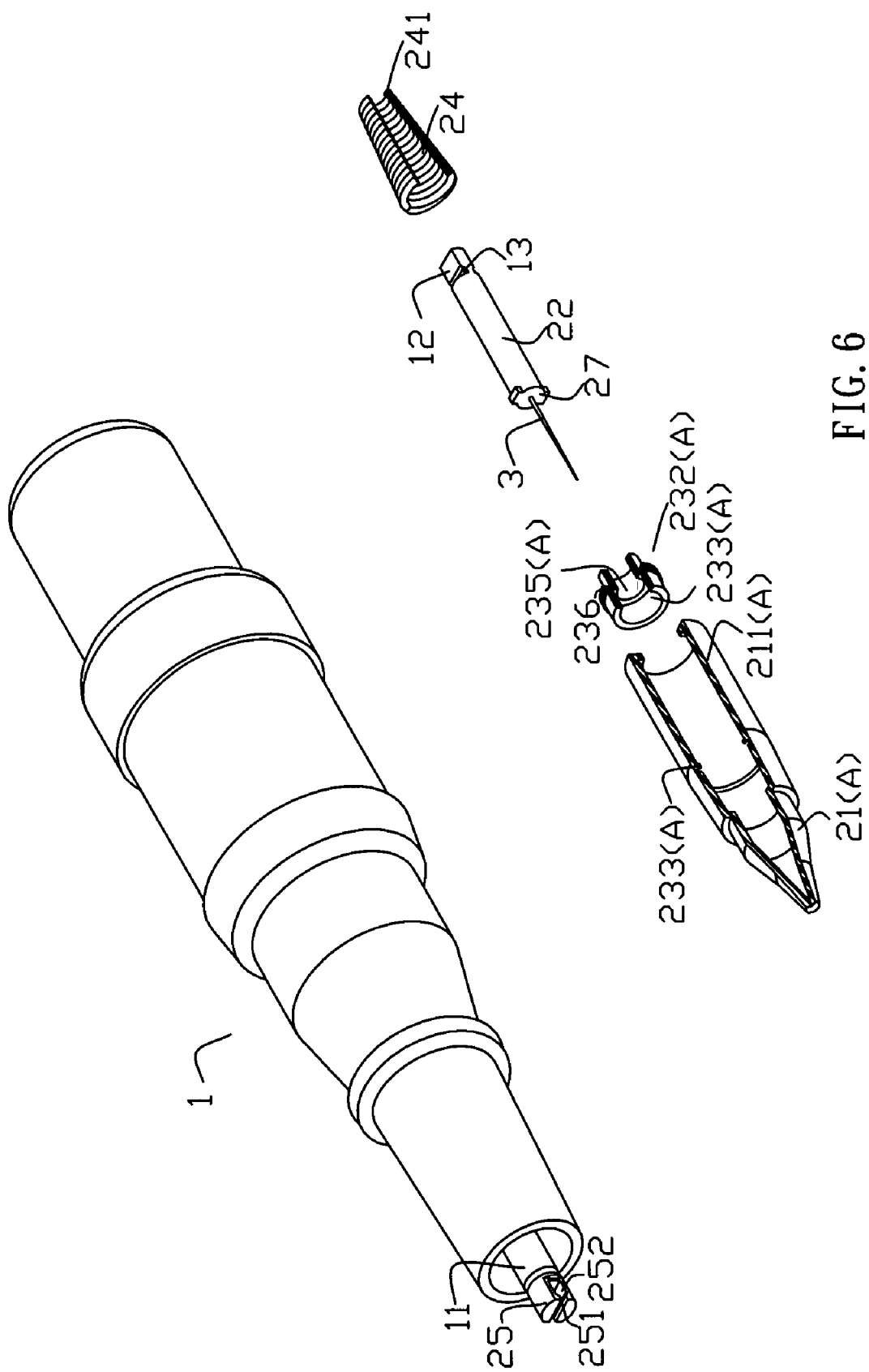
FIG. 6 is a structural exploded view of the second embodiment of the present invention.
Figure 7:
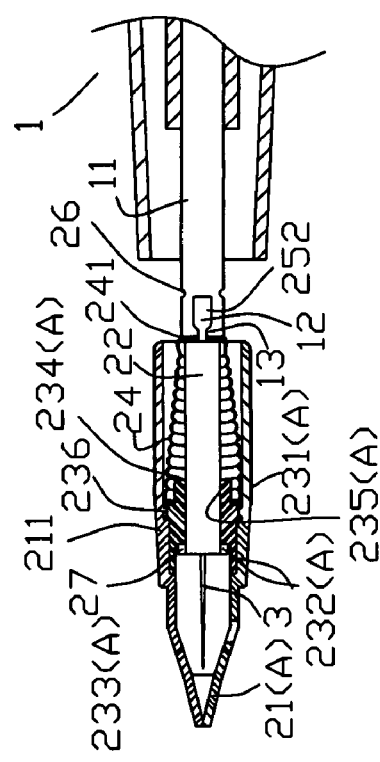
FIG. 7 is a schematic view showing the needle in the second embodiment of the present invention is not pushed outwards.
Figure 8:
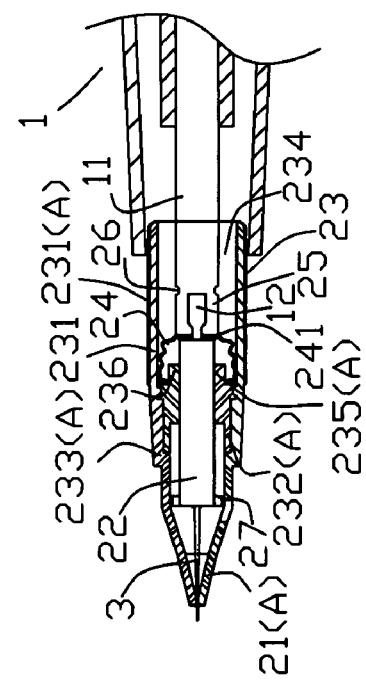
FIG. 8 is a schematic view showing the needle in the second embodiment of the present invention has been pushed outwards.

Referring to FIG. 6, another embodiment of the present invention is illustrated. In this embodiment, those identical to the above mentioned embodiment illustrated in FIGS. 1, 2 and 3 will not be further described herein. Only those difference are disclosed. The identical elements are identified by the same numerals. In this embodiment, the holding cover 23 and needle cover 21 are formed as an integral body. The needle cover 21A has a structure as the holding cover 23. The needle seat 232A is an independent structure. The needle clamper 22 of the needle 3 is received in the hole 235 in the needle seat 232A. Normally, the needle clamper 22 is received in the hole 235 of the needle cover 21A and resists against a rear surface of the needle seat 232A by using a telescopic element 24. The embedding portion 241 of the telescopic element 24 is embedded into the annular trench 26 of the needle clamper 22, as shown in FIG. 7. Thereby when the needle clamper 22 is pushed outwards, the telescopic element 24 provides a return force to the needle clamper 22, as shown in FIG. 8. The structure provides a tight seal to the safety needle assembly 2 and the body 1 so that the dye will not return.

Moreover, the needle seat 232A has an annular trench 236 which can be engaged to an annular ring 211 at an inner wall of the needle cover 21A so as to have the preferred positioning effect.

In the embodiment of the present invention, the two ends of the telescopic element 24 are thicker than a middle section of the telescopic element 24. Thus, in the pushing operation, the thin middle section can be compressed to generate elastic resilient force.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A safety needle device for tattooing body and eyebrows comprising;
    a body;
    a needle;
    a needle cover for receiving the needle;
    a holding cover combinable to a rear end of the needle cover;
    a needle clamper received in the holding cover for clamping the needle at one end and engaged to the body at another end thereof; and
    a telescopic element installed between the holding cover and a rear end of the needle clamper; and
    wherein the holding cover has an outer tube for being held by users; a needle seat is installed within the outer tube; the needle seat divides the outer tube into a first chamber and a second chamber; a hole is formed in the needle seat for communicating the first chamber and second chamber; the needle clamper is movable in the hole; the first chamber serves for combining the needle cover; the second chamber serves for receiving the telescopic movement of the needle so as to combine with the body.

2. The safety needle device for tattooing body and eyebrows as claimed in claim 1, wherein one end of the needle clamper serves to clamp the needle and opposite end of the needle clamper received in the second chamber and has a combining block; two wedge recesses are formed at two sides of a connection area between the combining block and the needle clamper.

3. The safety needle device for tattooing body and eyebrows as claimed in claim 2, wherein at least one limiting block is formed at the needle clamper at one end near the needle for controlling the needle to move forwards to expose out or to move backwards for storage; when the needle clamper retracts into the first chamber to a rearmost position, the two limiting blocks resist against a wall of the needle seat at the first chamber.

4. The safety needle device for tattooing body and eyebrows as claimed in claim 1, wherein the telescopic element is an elastic element which is compressible; two ends of the telescopic element has a larger size and resists against one end surface of the needle seat at the holding cover; another end of the telescopic element has a smaller size and has an embedding portion which can be embedded into the embedding groove of the needle clamper so that dye can be sealed without draining out from the second chamber.

5. The safety needle device for tattooing body and eyebrows as claimed in claim 1, wherein the telescopic element has a wavelike shape which is compressible; two ends of the telescopic element has a larger size and resists against one end surface of the needle seat at the holding cover; another end of the telescopic element has a smaller size and has an embedding portion which can be embedded into the embedding groove of the needle clamper so that dye can be sealed without draining out from the second chamber.

6. The safety needle device for tattooing body and eyebrows as claimed in claim 1, wherein the body has a joint; one end of the joint has a combining portion and an annular trench between the combining portion and the joint.

7. The safety needle device for tattooing body and eyebrows as claimed in claim 1, wherein in the unused state, the needle and the needle clamper are received within the needle cover.

8. The safety needle device for tattooing body and eyebrows as claimed in claim 1, wherein an interior of the needle cover is formed with a protecting space for receiving the needle.

* * * * *